United States Patent [19]

Cottman et al.

[11] Patent Number: 5,371,289

[45] Date of Patent: Dec. 6, 1994

[54] PREPARATION OF N-SUBSTITUTED-N'-PHENYL P-PHENYLENEDIAMINES

[75] Inventors: Kirkwood S. Cottman, Akron; Joseph A. Kuczkowski, Munroe Falls, both of Ohio

[73] Assignee: The Goodyear Tire & Rubber Company, Akron, Ohio

[21] Appl. No.: 34,953

[22] Filed: Mar. 22, 1993

[51] Int. Cl.$^5$ .................................. C07C 209/22
[52] U.S. Cl. .................................. 564/396; 564/434
[58] Field of Search ............... 564/396, 397, 433, 434, 564/435

[56] References Cited

U.S. PATENT DOCUMENTS 4,968,843  11/1990  Cottman ........................ 564/397
5,053,540  10/1991  Cottman ........................ 564/397

FOREIGN PATENT DOCUMENTS 125343  10/1981  Japan .

OTHER PUBLICATIONS

Radel et al, Industrial Engineering Chemical Products Res. Dev. 1982, 21, 566–570.
Gelling et al, Plastics and Rubber:Processing, Sep. 1977, pp. 83–86.
Chemical Abstracts FR 2659-650-A, week 9148 (1991).
Chemical Abstracts FR 2659-651-A, week 9148 (1991).
Chemical Abstracts EP 452-168-A, week 9142 (1991).

*Primary Examiner*—Gary E. Hollinden
*Assistant Examiner*—Brian M. Burn
*Attorney, Agent, or Firm*—Bruce J. Hendricks

[57] ABSTRACT

The present invention relates to a process for the preparation of a N-substituted-N'-phenyl-p-phenylenediamine of the formula:

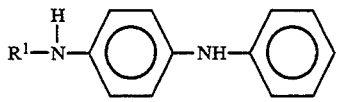

comprising reacting (a) a mixture of (1) N-phenyl-p-quinoneimine of the formula:

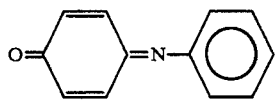

and (2) p-hydroxydiphenylamine in a mole ratio of N-phenyl-p-quinoneimine to p-hydroxydiphenylamine of from 1.5:1 to 1:1.5 with (b) a primary amine of the formula:

$R^1-NH_2$ in the presence of methanol wherein $R^1$ is selected from the group of radicals consisting of alkyls having 1 to 20 carbon atoms, cycloalkyls having 6 to 8 carbon atoms and radicals of the structural formula:

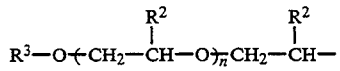

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6.

12 Claims, No Drawings

PREPARATION OF N-SUBSTITUTED-N'-PHENYL P-PHENYLENEDIAMINES

BACKGROUND OF THE INVENTION

The present invention relates to an unique method for preparing N-substituted-N'-phenyl-p-phenylenediamines from a mixture of N-phenyl-p-quinoneimine and p-hydroxydiphenylamine. N-substituted-N'-phenyl-p-phenylenediamines are useful as in the production of drugs, agricultural products, and useful as dyes, antioxidants, antiozonants, gel inhibitors and polymerization inhibitors for rubber.

N-substituted-N'-phenyl-p-phenylenediamines have been made by a variety of methods known to those skilled in the art. For example, Japanese Application 125343-1981 discloses a process for the preparation of phenylenediamines or its N-substitution product by reacting aminophenol or its N-substitution product with (a) ammonia, primary amine or secondary amine in the presence of an acidic catalyst and polycyclic aromatic compound. The process disclosed in Japanese Application No. 125343-1981 is characterized by a one step, one pot procedure and suggests via gas chromatography that yields are upwards to 50 percent. However, preparation of the products by this procedure would necessitate the use of elaborate distillation equipment to remove the polycyclic aromatic compounds that are employed. The removal of the polycyclic aromatic compounds further contributes to the expense of manufacturing the N-substituted-N'-phenylphenylenediamine. U.S. Pat. No. 4,968,843 discloses a process for the preparation of a N-substituted-N'-phenyl-p-phenylenediamine. The process in this patent involves reacting N-phenyl-p-quinoneimine with a primary amine. This patent teaches that the N-phenyl-p-quinoneimine reactant should not contain more than 5 weight percent p-hydroxydiphenylamine and preferably no or only trace amounts are present. The patent teaches that with an increasing amount of p-hydroxydiphenylamine, there is an increasing hinderance of the reaction to yield the N-substituted-N'-phenyl-p-phenylenediamine. Since demand for N-substituted-N'-phenyl-p-phenylenediamines is on the increase with their wide-spread applications, there is a need for a new and more efficient process for their production.

SUMMARY OF THE INVENTION

The present invention relates to a process for the preparation of N-substituted-N'-phenyl-p-phenylenediamines by reacting (a) a reaction mixture of (1) N-phenyl-p-quinoneimine and (2) p-hydroxydiphenylamine with (b) a primary amine.

DETAILED DESCRIPTION OF THE PREFERRED EMBODIMENTS

There is disclosed a process for the preparation of a N-substituted-N'-phenyl-p-phenylenediamine of the formula:

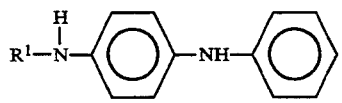

comprising reacting (a) a mixture of (1) N-phenyl-p-quinoneimine of the formula:

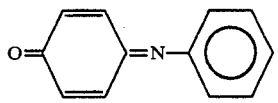

and (2) p-hydroxydiphenylamine in a mole ratio of N-phenyl-p-quinoneimine to p-hydroxydiphenylamine of from 1.5:1 to 1:1.5 with (b) a primary amine of the formula:

$$R^1-NH_2$$

in the presence of methanol and wherein $R^1$ is selected from the group of radicals consisting of alkyls having 1 to 20 carbon atoms, cycloalkyls having 6 to 8 carbon atoms and radicals of the structural formula:

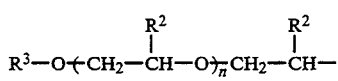

wherein $R^2$ may be the same or different and is independently selected from the group of radicals consisting of hydrogen and an alkyl having 1 carbon atom, R3 is selected from the group of radicals consisting of an alkyl having 1 to 12 carbon atoms and n is an integer of from 0 to 6.

With respect to the above formulae, preferably $R^1$ is selected from the group of radicals consisting of alkyls having 3 to 8 carbon atoms and cycloalkyls having 6 carbon atoms.

The starting materials for the reaction are N-phenyl-p-quinoneimine, p-hydroxydiphenylamine, and the primary amine. The mole ratio of the N-phenyl-p-quinoneimine and the p-hydroxydiphenylamine should range from 1.5:1 to 1:1.5. Preferably, the mole ratio will range around 1:1.

The p-hydroxydiphenylamine used in the reaction has two functions. The N-phenyl-p-quinoneimine reacts with the primary amine to produce a N-alkyl-N'-phenyl-p-quinonediimine. The p-hydroxydiphenylamine then reduces the N-alkyl-N'-phenyl-p-quinonediimine to its corresponding N-alkyl-N'-phenyl-p-phenylenediamine, while the p-hydroxydiphenylamine itself is oxidized to additional N-phenyl-p-quinoneimine.

The N-phenyl-p-quinoneimine may be prepared by the simple oxidation of p-hydroxydiphenylamine. For example, the p-hydroxydiphenylamine may be dissolved in a suitable solvent and oxidized. Examples of solvents which may be used include acetone, methylisobutylketone, methylenechloride, tetrahydrofuran and toluene. Preferably a water soluble solvent is used such as the acetone. The p-hydroxyphenylamine is oxidized with an oxidizing agent. Representative oxidizing agents include sodium dichromate or potassium dichromate in conjunction with an acid, such as acetic acid. The reaction temperature of the oxidation reaction may vary but is generally from about 20° C. to about 100° C. The preferred reaction temperature ranges from about 25° C. to about 70° C.

Typically the oxidation reaction may be conducted by dissolving the p-hydroxydiphenylamine in a solvent such as acetone followed by the addition of acetic acid. Aqueous potassium or sodium dichromate is then added between 20° and 50° C. The molar ratio of p-hydroxydiphenylamine to $Cr_2O_7$ is from about 7:1 to 1:3. Preferably a molar ratio of 2:1 to 1:1 is used. A sufficient amount of acid should be present to solubilize the dichromate. Operable amounts of acid based on the moles of p-hydroxydiphenylamine range from about 2:1 to 1:3 of p-hydroxydiphenylamine to moles of acid (based on H+). The N-phenyl-p-quinoneimine product forms instantaneously and can be isolated by adding the oxidation solution to excess cold water. The precipitated product is then filtered, washed with water and dried. Other suitable means known in the art may be used for preparing N-phenyl-p-quinoneimine.

The mixture of N-phenyl-p-quinoneimine and p-hydroxydiphenylamine is reacted with a primary amine. Examples of suitable amines which may be used in the present invention include methylamine, ethylamine, propylamine, isopropylamine, n-butylamine, sec-butylamine, n-pentylamine, 1-methylbutylamine, 1,2-dimethylpropylamine, 2-methylbutylamine, 3-methylbutylamine, 1-ethylpropylamine, n-hexylamine, 1-methylheptylamine, 1-methylpentylamine, 2-methylpentylamine, 3-methylpentylamine, 4-methylpentylamine, 1,2-dimethylbutylamine, 1,3-dimethylbutylamine, 1-ethylbutylamine, 2-ethylbutylamine, heptylamine, octylamine, nonylamine, decylamine, cyclohexylamine, methylcyclohexylamine, benzenamine(aniline) and cyclooctylamine. Of the above amines, isopropylamine, 1,3-dimethylbutylamine and cyclohexylamine are preferred.

Additional primary amines which may be used in the present invention are of the formula:

wherein $R^1$ is represented by:

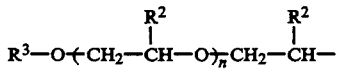

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6. Examples of amines of the above formula are commercially available from Texaco Chemical Company under the trademark JEFFAMINE®. A specific example of such product includes JEFFAMINE® M-89 having the formula:

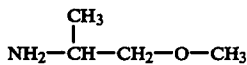

The molar ratio of the mixture of N-phenyl-p-quinoneimine and p-hydroxydiphenylamine to the primary amine in the reaction mixture may vary. Generally speaking, the molar ratio of the mixture of N-phenyl-p-quinoneimine and p-hydroxydiphenylamine to the primary amine ranges from about 1:1 to about 1:10, with a ratio of from about 1:1 to about 1:3 being preferred.

The reaction of the mixture of N-phenyl-p-quinoneimine and p-hydroxydiphenylamine with the primary amine must be conducted in the presence of a methanol. Preferably, the only solvent is methanol, however, minor amounts of water may be present in addition to the methanol so long as the reactants remain solubilized in the methanol. Use of solvents such as methylene chloride and tetrahydrofuran will result in significantly decreased yields of desired product. The purpose of the methanol is to solubilize the reactants at the reaction temperature. Therefore, the minimal amount required need be sufficient to solubilize the reactants.

The reaction between the mixture of N-phenyl-p-quinoneimine and p-hydroxydiphenylamine with the primary amine may be conducted at a variety of temperatures. Generally speaking, the temperature of the reaction ranges from about 15° C. to about 130° C. with a range of about 20° C. to about 110° C. being preferred. Because the boiling point of methanol is 65° C. at sea level, if one desires to run the reaction in excess of 65° C., one must run the reaction in a closed system. In a particularly preferred embodiment, the reaction is conducted between room temperature and 65° C.

Examples of N-substituted-p-phenylenediamines which may be prepared according to the present invention include
N-methyl-N'-phenyl-p-phenylenediamine,
N-ethyl-N'-phenyl-p-phenylenediamine,
N-propyl-N'-phenyl-p-phenylenediamine,
N-isopropyl-N'-phenyl-p-phenylenediamine,
N-n-butyl-N'-phenyl-p-phenylenediamine,
N-sec-butyl-N'-phenyl-p-phenylenediamine,
N-n-pentyl-N'-phenyl-p-phenylenediamine,
N-1-methylbutyl-N'-phenyl-p-phenylenediamine,
N-(1-methylheptyl)-N'-phenyl-p-phenylenediamine,
N-1,2-dimethylpropyl-N'-phenyl-p-phenylenediamine,
N-2-methylbutyl-N'-phenyl-p-phenylenediamine,
N-3-methylbutyl-N'-phenyl-p-phenylenediamine,
N-1-ethylpropyl-N'-phenyl-p-phenylenediamine,
N-n-hexyl-N'-phenyl-p-phenylenediamine,
N-1-methylpentyl-N'-phenyl-p-phenylenediamine,
N-2-methylpentyl-N'-phenyl-p-phenylenediamine,
N-3-methylpentyl-N'-phenyl-p-phenylenediamine,
N-4-methylpentyl-N'-phenyl-p-phenylenediamine,
N-1,2-dimethylbutyl-N'-phenyl-p-phenylenediamine,
N-1,3-dimethylbutyl-N'-phenyl-p-phenylenediamine,
N-1-ethylbutyl-N'-phenyl-p-phenylenediamine,
N-2-ethylbutyl-N'-phenyl-p-phenylenediamine,
N-heptyl-N'-phenyl-p-phenylenediamine,
N-octyl-N'-phenyl-p-phenylenediamine,
N-nonyl-N'-phenyl-p-phenylenediamine,
N-decyl-N'-phenyl-p-phenylenediamine,
N-cyclooctyl-N'-phenyl-p-phenylenediamine,
N-cyclohexyl-N'-phenyl-p-phenylenediamine,
N-methylcyclohexyl-N'-phenyl-p-phenylenediamine, and
N-cyclooctyl-N'-phenyl-p-phenylenediamine.

Preferably, the N-substituted phenylenediamine is
N-(1,3-dimethylbutyl)-N'-phenyl-p-phenylenediamine,
N-isopropyl-N'-phenyl-p-phenylenediamine,
N-(1-methylheptyl)-N'-phenyl-p-phenylenediamine, and
N-cyclohexyl-N'-phenyl-p-phenylenediamine.

The reaction between the mixture of N-phenyl-p-quinoneimine and p-hydroxydiphenylamine with the primary amine may be in the presence of or absence of an acidic catalyst. Examples of acid catalysts include methanesulfonic acid, toluenesulfonic acid and the like.

Following the reaction between the mixture of N-phenyl-p-quinoneimine and the p-hydroxydiphenylamine with the primary amine, the product can be used as is for the stabilization of rubber. If minor amounts are present and one wants to further increase the amount of yield of the desired product, the reaction mixture may be hydrogenated. The reaction mixture is hydrogenated to convert the diimines to the desired N-substituted-N'-phenyl-p-phenylenediamines.

Representative catalysts for the hydrogenation reaction are platinum on carbon, palladium on carbon, Girdler G-22 copper chromite-barium promoted, aqueous sodium hydrosulfite and the like. High temperatures and pressures may be required if the Girdler G-22 catalyst is used. The hydrogenation is preferably done near room temperature with palladium on carbon.

The following examples are included for purposes of illustrating but not limiting the present invention.

EXAMPLE 1

Preparation of N-(1,3-dimethylbutyl)-N'-phenyl-p-phenylenediamine

Into a 120 ml reaction vessel equipped with a thermometer was dissolved 2.5 grams (0.5 mole eq) of p-hydroxydiphenylamine (HDPA) and 2.5 grams (0.5 mole eq) of N-phenyl-p-quinoneimine (QI) in 25 grams of methanol at 54° C. Then to the slurry was added 4.8 grams (1.5 mole eq.) of 1,3-dimethylbutylamine. The reaction vessel was maintained at 55° C. while the vessel sat in an ultrasonic bath for the 4½ hours. The reaction product was sampled periodically for area percent gas chromatographic analysis as shown in Table 1. The respective amounts of QI, HDPA, N-(1,3-dimethylbutyl)-N'-phenyl-p-quinonediimine (QDI) and N-(1,3-dimethylbutyl)-N'-phenyl-p-phenylenediamine (Product) are listed in Table 1.

TABLE 1

| Compound | Example 1 | | | | | | | |
|---|---|---|---|---|---|---|---|---|
| | 15' | 30' | 60' | 90' | 120' | 180' | 240' | 300' |
| QI | 28.9 | 23.0 | 14.5 | 11.0 | 8.4 | — | 3.1 | 2.2 |
| HDPA | 20.0 | 10.2 | 4.0 | 1.3 | 0.6 | — | — | — |
| QDI | — | — | — | — | 1.2 | 4.8 | 4.7 | 4.8 |
| Product | 49.2 | 64.6 | 76.9 | 81.9 | 84.9 | 85.4 | 87.0 | 88.5 |
| Unknowns | 2.0 | 2.3 | 4.4 | 4.8 | 4.8 | 4.6 | 5.1 | 5.4 |

EXAMPLE 2

The procedures of Example 1 were repeated; however, the (1) mole ratios of N-phenylquinoneimine to hydroxydiphenylamine; (2) solvent and (3) primary amine were varied. Table 2 below provides the variables for each sample. Tables 3–14 provide the resulting area percent gas chromatographic analysis for a given time for each sample.

TABLE 2

| | Starting Material | | | Product | | |
|---|---|---|---|---|---|---|
| Sample | QI | HDPA | Primary Amine | Temperature of Reaction °C. | Product Data | Solvent |
| Control 1 | 1 mole | 0 | 1.25 mole 1,3-dimethylbutylamine | 55° C. | Table 3 | MeOH |
| Control 2 | 1 mole | 0 | 1.50 mole 1,3-dimethylbutylamine | 65° C. | Table 4 | MeOH |
| Control 3 | 0.75 mole | 0.25 mole | 1.25 mole 1,3-dimethylbutylamine | 54° C. | Table 5 | MeOH |
| Control 4 | 0.75 mole | 0.25 mole | 1.75 mole 1,3-dimethylbutylamine | 75° C. | Table 6 | Toluene |
| Control 5 | 0.65 mole | 0.35 mole | 2.0 mole 1,3-dimethylbutylamine | 54° C. | Table 7 | MeOH/H2O |
| 6 | 0.55 mole | 0.45 mole | 2.0 mole 1,3-dimethylbutylamine | 54° C. | Table 8 | MeOH/H2O |
| Control 7 | 0.5 mole | 0.5 mole | 1.4 mole 1,3-dimethylbutylamine | 54° C. | Table 9 | DMF |
| Control 8 | 0.5 mole | 0.5 mole | 2.0 mole 1,3-dimethylbutylamine | 100° C. | Table 10 | Toluene |
| 9 | 0.5 mole | 0.5 mole | 1.5 mole 1,3-dimethylbutylamine | 60° C. | Table 11 | MeOH |
| 10 | 0.5 mole | 0.5 mole | 1.2 mole cyclohexylamine | 54° C. | Table 12 | MeOH |
| 11 | 0.48 mole | 0.52 mole | 1.5 mole 1,3-dimethylbutylamine | 54° C. | Table 13 | MeOH/H2O |
| 12 | 0.40 mole | 0.60 mole | 2.0 mole 1,3-dimethylbutylamine | 54° C. | Table 14 | MeOH |
| Control 13 | 0.25 mole | 0.75 mole | 2.0 mole 1,3-dimethylbutylamine | 54° C. | Table 15 | MeOH |

TABLE 3

| Compound | Example 2 Sample 1 | | | | | | |
|---|---|---|---|---|---|---|---|
| | 15' | 30' | 60' | 90' | 120' | 180' | 240' |
| QI | 41.8 | 21.8 | 6.5 | 3.4 | 1.2 | — | — |
| HDPA | — | — | — | — | — | — | — |
| QDI | 39.9 | 55.6 | 65.0 | 66.7 | 59.4 | 46.8 | 33.8 |
| Product | 16.9 | 21.2 | 22.9 | 25.6 | 31.6 | 41.6 | 51.6 |
| Unknowns | 1.3 | 1.8 | 5.8 | 4.3 | 8.3 | 12.6 | 14.6 |

TABLE 4

| Compound | Example 2 Sample 2 | | | |
|---|---|---|---|---|
| | 15' | 30' | 60' | 90' |
| QI | 19.7 | 5.9 | 1.5 | 1.1 |
| HDPA | — | — | — | — |
| QDI | 27.9 | 37.7 | 32.6 | 30.1 |
| Product | 50.4 | 53.0 | 56.6 | 58.6 |
| Unknowns | 2.5 | 3.4 | 6.2 | 9.4 |

TABLE 5

| Compound | Example 2 Sample 3 | | | | |
|---|---|---|---|---|---|
| | 15' | 30' | 60' | 90' | 120' | 180' |
| QI | 35.5 | 25.2 | 18.2 | 10.8 | 7.4 | 4.2 |
| HDPA | 9.4 | 3.6 | 0.9 | 0.4 | — | — |
| QDI | — | 0.5 | 5.2 | 7.9 | 8.4 | 7.8 |
| Product | 55.4 | 66.9 | 71.9 | 75.0 | 78.0 | 78.5 |
| Unknowns | 1.8 | 2.1 | 4.3 | 5.9 | 6.2 | 9.5 |

TABLE 6

| Compound | \multicolumn{6}{c}{Example 2 Sample 4} |
|---|---|---|---|---|---|---|
| | 15' | 30' | 60' | 90' | 120' | 180' |
| QI | 44.7 | 39.0 | 24.7 | 19.9 | 14.6 | 7.7 |
| HDPA | 45.9 | 43.3 | 36.4 | 33.8 | 30.1 | 29.1 |
| QDI | — | — | — | — | — | — |
| Product | 7.7 | 15.4 | 30.7 | 36.8 | 43.5 | 49.5 |
| Unknowns | 1.7 | 2.4 | 8.3 | 9.4 | 11.7 | 13.6 |

TABLE 7

| Compound | \multicolumn{5}{c}{Example 2 Sample 5} |
|---|---|---|---|---|---|
| | 15' | 30' | 60' | 90' | 120' |
| QI | 37.8 | 26.7 | 10.6 | 6.5 | 3.3 |
| HDPA | 6.0 | .6 | — | — | — |
| QDI | — | 4.5 | 15.8 | 21.1 | 19.8 |
| Product | 54.0 | 65.2 | 67.9 | 68.3 | 70.1 |
| Unknowns | 2.2 | 3.1 | 5.7 | 4.2 | 6.7 |

TABLE 8

| Compound | \multicolumn{6}{c}{Example 2 Sample 6} |
|---|---|---|---|---|---|---|
| | 15' | 30' | 60' | 90' | 120' | 180' |
| QI | 30.6 | 22.7 | 13.5 | 9.6 | 5.4 | 3.1 |
| HDPA | 14.2 | 5.9 | 0.8 | — | — | — |
| QDI | — | — | 2.0 | 5.3 | 5.8 | 9.0 |
| Product | 53.3 | 68.4 | 81.3 | 79.6 | 85.2 | 81.5 |
| Unknowns | 2.0 | 2.0 | 2.3 | 5.5 | 3.5 | 6.3 |

TABLE 9

| Compound | \multicolumn{5}{c}{Example 2 Sample 7} |
|---|---|---|---|---|---|
| | 15' | 30' | 60' | 90' | 120' |
| QI | 40.1 | 27.1 | 13.6 | 4.7 | 3.3 |
| HDPA | 51.7 | 58.3 | 63.9 | 67.4 | 69.4 |
| QDI | — | — | — | — | — |
| Product | 3.2 | 5.8 | 8.1 | 9.3 | 10.1 |
| Unknowns | 4.9 | 8.7 | 14.4 | 15.8 | 15.9 |

TABLE 10

| Compound | \multicolumn{6}{c}{Example 2 Sample 8} |
|---|---|---|---|---|---|---|
| | 15' | 30' | 60' | 90' | 120' | 180' |
| QI | 41.4 | 32.1 | 24.7 | 14.9 | 10.1 | 3.9 |
| HDPA | 46.7 | 45.5 | 38.5 | 37.6 | 34.7 | 33.9 |
| QDI | — | — | — | — | — | — |
| Product | 11.2 | 20.9 | 34.8 | 45.7 | 48.4 | 53.7 |
| Unknowns | .8 | 1.5 | 1.8 | 1.7 | 6.8 | 8.6 |

TABLE 11

| Compound | \multicolumn{7}{c}{Example 2 Sample 9} |
|---|---|---|---|---|---|---|---|
| | 15' | 30' | 60' | 90' | 120' | 180' | 240' |
| QI | 16.4 | 9.3 | 7.8 | 4.3 | 2.4 | 2.9 | 1.9 |
| HDPA | 25.6 | 20.0 | 13.8 | 13.3 | 13.1 | 12.2 | 11.3 |
| QDI | — | — | — | — | — | — | — |
| Product | 56.2 | 68.7 | 76.5 | 80.8 | 81.5 | 82.4 | 84.6 |
| Unknowns | 1.8 | 2.0 | 1.9 | 1.6 | 3.0 | 2.6 | 2.1 |

TABLE 12

| Compound | 15' | 60' |
|---|---|---|
| QI | 1.5 | — |
| HDPA | 2.7 | — |
| QDI | — | — |
| Product | 87.7 | 90.3 |
| Unknowns | 8.1 | 9.7 |

TABLE 13

| Compound | \multicolumn{7}{c}{Example 2 Sample 10} |
|---|---|---|---|---|---|---|---|
| | 15' | 30' | 60' | 90' | 120' | 180' | 240' |
| QI | 18.6 | 12.1 | 6.2 | 5.1 | 3.5 | 1.8 | 1.3 |
| HDPA | 23.9 | 15.6 | 12.3 | 11.5 | 9.3 | 6.4 | 6.9 |
| QDI | — | — | — | — | — | — | — |
| Product | 55.1 | 67.0 | 76.2 | 78.0 | 80.0 | 84.1 | 83.5 |
| Unknowns | .6 | 2.5 | 5.1 | 5.3 | 7.1 | 7.7 | 7.5 |

TABLE 14

| Compound | \multicolumn{6}{c}{Example 2 Sample 11} |
|---|---|---|---|---|---|---|
| | 15' | 30' | 60' | 90' | 120' | 180' |
| QI | 6.9 | 5.8 | 0.7 | — | — | — |
| HDPA | 34.3 | 23.8 | 15.2 | 12.2 | 10.0 | 9.6 |
| QDI | — | — | — | — | — | — |
| Product | 56.4 | 66.2 | 79.5 | 83.1 | 83.4 | 84.3 |
| Unknowns | 4.8 | 7.0 | 7.8 | 6.8 | 8.7 | 7.2 |

TABLE 15

| Compound | \multicolumn{5}{c}{Example 2 Sample 12} |
|---|---|---|---|---|---|
| | 15' | 30' | 60' | 90' | 120' |
| QI | 5.2 | 3.2 | 1.2 | 0.6 | 4.8 |
| HDPA | 48.5 | 40.9 | 38.6 | 39.1 | 33.7 |
| QDI | — | — | — | — | — |
| Product | 45.2 | 53.9 | 57.4 | 57.9 | 59.0 |
| Unknowns | 1.1 | 1.9 | 3.0 | 2.4 | 2.4 |

The reaction conditions listed in Table 2 in combination with the specific tables for each sample demonstrate the significance of the QI/HDPA ratio as well as the solvent in achieving large yields of the N-substituted-N'-phenyl-p-phenylenediamines.

What is claimed is:

1. A process for the preparation of a N-substituted-N'-phenyl-p-phenylenediamine of the formula:

$$R^1-\underset{H}{N}-\phenyl-NH-\phenyl$$

comprising reacting (a) a mixture of (1) N-phenyl-p-quinoneimine of the formula:

$$O=\phenyl=N-\phenyl$$

and (2) p-hydroxydiphenylamine in a mole ratio of N-phenyl-p-quinoneimine to p-hydroxyphenylamine of from 1.5:1 to 1:1.5 with (b) a primary amine of the formula:

$$R^1-NH_2$$

in the presence of methanol and wherein $R^1$ is selected from the group of radicals consisting of alkyls having 1 to 20 carbon atoms, cycloalkyls having 6 to 8 carbon atoms, and radicals of the structural formula:

$$R^3-O+CH_2-\underset{R^2}{\overset{|}{C}H}-O)_n CH_2-\underset{R^2}{\overset{|}{C}H}-$$

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6.

2. The process of claim 1 wherein $R^1$ is selected from the group of radicals consisting of alkyls having 3 to 8 carbon atoms and cycloalkyls having 6 carbon atoms.

3. The process of claim 1 wherein said N-substituted-N'-phenyl-p-phenylenediamine is selected from the group consisting of
N-(1,3-dimethylbutyl)-N'-phenyl-p-phenylenediamine,
N-isopropyl-N'-phenyl-p-phenylenediamine,
N-(1-methylheptyl)-N'-phenyl-p-phenylenediamine,
N-cyclohexyl-N'-phenyl-p-phenylenediamine, and
N-(1-methyl-2-methoxyethyl)-N'-phenyl-p-phenylenediamine.

4. The process of claim 3 wherein said N-substituted-N'-phenyl-p-phenylenediamine is N-(1,3-dimethylbutyl)-N'-phenyl-p-phenylenediamine.

5. The process of claim 3 wherein said N-substituted-N'-phenyl-p-phenylenediamine is N-cyclohexyl-N'-phenyl-p-phenylenediamine.

6. The process of claim 1 wherein said reaction is conducted at temperature of from about 15° C. to about 65° C.

7. The process of claim 6 wherein said reaction is conducted at a temperature ranging from about 45° C. to 65° C.

8. The process of claim 6 wherein said reaction is conducted at room temperature.

9. The process of claim 1 wherein $R^3$ is an alkyl having 1 to 2 carbon atoms and n is 0 or 1.

10. The process of claim 1 wherein the mole ratio of the mixture of N-phenyl-p-quinoneimine and p-hydroxydiphenylamine to the primary amine ranges from about 1:1 to about 1:10.

11. The process of claim 1 wherein methanol is the sole solvent that is present.

12. The process of claim 1 wherein methanol and water are the sole solvents that are present.

* * * * *